(12) United States Patent
Song et al.

(10) Patent No.: US 7,476,540 B2
(45) Date of Patent: Jan. 13, 2009

(54) MONOCLONAL ANTIBODIES TO MESENCHYMAL STEM CELLS

(75) Inventors: Yeong-Wook Song, Seoul (KR); Hyun-Jung Yoo, Busan (KR); Sung-Soo Yoon, Seoul (KR); Seonyang Park, Seoul (KR); Weon-Seo Park, Goyang-si (KR); Dong-Jo Kim, Seoul (KR); Eun-Bong Lee, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 268 days.

(21) Appl. No.: 11/329,523

(22) Filed: Jan. 10, 2006

(65) Prior Publication Data

US 2007/0161050 A1     Jul. 12, 2007

(51) Int. Cl.
*C12N 5/00*     (2006.01)
*C07K 16/00*     (2006.01)

(52) U.S. Cl. .................................. 435/346; 530/388.15

(58) Field of Classification Search .................. None
See application file for complete search history.

(56) References Cited

U.S. PATENT DOCUMENTS 5,837,539 A     11/1998     Caplan et al.

OTHER PUBLICATIONS

Hyun-Jung Yoo et al., "Production and Characterization of Monoclonal Antibodies to Mesenchymal Stem Cells Derived from Human Bone Marrow," Hybridoma 24:92-97, 2005.

*Primary Examiner*—Michail A Belyavskyi
(74) *Attorney, Agent, or Firm*—Clark & Elbing LLP

(57) ABSTRACT

The present invention relates to monoclonal antibodies specifically binding to a membrane antigen of human mesenchymal stem cells, hybridoma cell lines producing the same, and methods for identifying or isolating human mesenchymal stem cells using the same. The monoclonal antibodies of this invention exhibit excellent specificity to human mesenchymal stem cells, inter alia, bone marrow-derived human mesenchymal stem cells, so that it allows for the identification and isolation of human mesenchymal stem cells with much higher specificity.

3 Claims, 4 Drawing Sheets

A

B

US 7,476,540 B2

MONOCLONAL ANTIBODIES TO MESENCHYMAL STEM CELLS

BACKGROUND OF THE INVENTION

1. Field of the Invention

The present invention relates to monoclonal antibodies specifically binding to a membrane antigen of human mesenchymal stem cells, hybridoma cell lines producing the same, and methods for identifying or isolating human mesenchymal stem cells using the same.

2. Description of the Related Art

Hemopoiesis is sustained by two main cellular components, hematopoietic cells and mesenchymal stem cells (MSCs).[1,2] MSCs are multipotent and are the precursors of marrow stroma, bone, cartilage, muscle and connective tissue. MSCs isolated from bone marrow have been shown to have multilineage potential and have been utilized experimentally in cell-based therapies.[3,4] Human bone marrow (BM) has been shown to contain MSCs that fabricate the connective tissue network of the marrow, called the stroma.[5] MSCs may have an important role in the repair of musculoskeletal tissues, and can differentiate into osteoblasts,[6] chondrocytes,[7] adipocytes,[3] tenocytes,[8] and myocytes.[9] Although MSCs are present in very small numbers in the bone marrow, they are capable of substantial proliferation and expansion in culture.[10,11] Undifferentiated MSCs exhibit a fibroblast-like morphology and have a characteristic pattern of cell-surface antigen expression.[12] the present invention we developed methods for isolating and culturing MSCs from human bone marrow aspirates and found that these cultured cells display a fibroblastic morphology and retain their pluripotentiality following extensive culture expansion.[13,14] MSCs are characterized phenotypically in humans as non-hematopoietic cells, since they do not express CD34 or CD45.[3] Characteristic markers for expanded MSCs have been reported and designated as SH2, SH3, and SH4.[15] However, none of these markers are specific for MSCs, which hampers the isolation of pure MSC populations. In addition, there are no antibodies specifically bound to MSCs.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Under such circumstances, the present inventors have made intensive research to develop a novel monoclonal antibody to specifically detect human mesenchymal stem cells, and as a result, developed a monoclonal antibody specifically binding to a membrane protein antigen of human mesenchymal stem cells and verified its specificity to human mesenchymal stem cells, inter alia, bone marrow-derived human mesenchymal stem cells.

Accordingly, it is an object of this invention to provide a monoclonal antibody specifically binding to a membrane protein antigen of human mesenchymal stem cells.

It is another object of this invention to provide a hybridoma cell line producing a monoclonal antibody specifically binding to a membrane protein antigen of human mesenchymal stem cells.

It is still another object of this invention to provide a method for identifying or isolating human mesenchymal stem cells.

It is further object of this invention to provide a kit for identifying or isolating human mesenchymal stem cells.

Other objects and advantages of the present invention will become apparent from the detailed description to follow and together with the appended claims and drawings.

DETAILED DESCRIPTION OF THIS INVENTION

Figure 1:
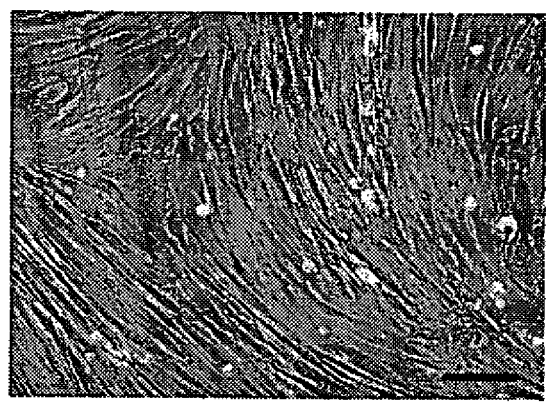
FIG. 1 represents morphological and phenotypic characterizations of human mesenchymal stem cells. (A) Culture-expanded mesenchymal stem cells (MSCs) showed a spindle-shaped fibroblastic morphology after culture expansion under a phase contrast microscope. Scale bar=100 μm, Original magnification, ×100. (B) Isolated cultured MSCs were negative for CD34 but positive for CD105 and CD166 by flow cytometry.
Figure 1:
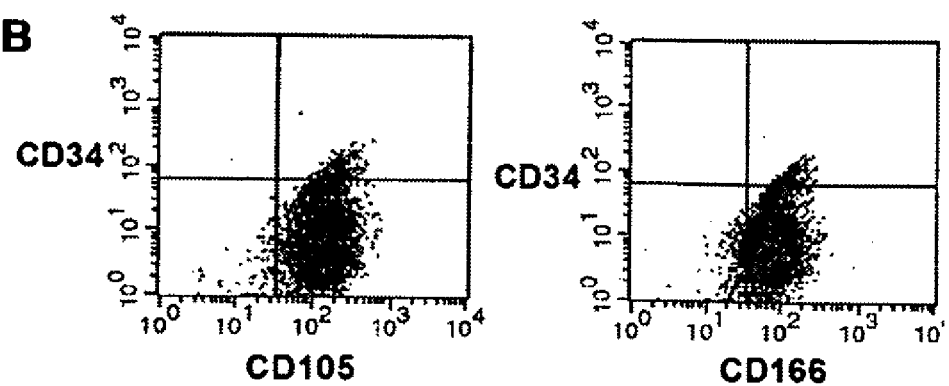

In one aspect of this invention, there is provided a monoclonal antibody specifically binding to a membrane protein antigen of human mesenchymal stem cells, which is produced by a hybridoma cell line as deposited with the Korean Cell Line Research Foundation (Cancer Research Institute, Seoul National University, College of Medicine, 28 Yongondong, Chongno-Gu, Seoul, 110-744, Korea) under Accession Nos. KCLRF-BP-000123, KCLRF-BP-000124 or KCLRF-BP-000125 on Dec. 10, 2005.

In another aspect of this invention, there is provided a hybridoma cell line producing the antibody of claim 1, which is deposited with the Korean Cell Line Research Foundation (Cancer Research Institute, Seoul National University, College of Medicine, 28 Yongondong, Chongno-Gu, Seoul, 110-744, Korea) under Accession Nos. KCLRF-BP-000123, KCLRF-BP-000124 or KCLRF-BP-000125 on Dec. 10, 2005.

Monoclonal antibodies (MAbs) are useful tools in many fields of biology and medical research for diagnostic and therapeutic applications. In previous reports, mesenchymal stem cells (MSCs) were found to be difficult to isolate and were usually contaminated by hematopoietic precursors.[5,17] Moreover, MSCs immunoselected using specific surface markers show heterogeneous morphologies, surface marker profiles, and phenotypes.[18-21] Thus, the production of MAbs against derived MSCs would allow the characterization of MSC proteins by ELISA, immunofluorescence staining, flow cytometry and Western blotting.

The present invention is directed to MAbs specifically binding to a membrane antigen of human MSCs, serving as human MSC marker immunosensors, and hybridoma cell lines producing the same. In particular, MAbs of the present invention specifically binds to a membrane antigen of human MSCs derived from bone marrow.

The MAbs of the present invention are manufactured using antigens prepared from MSCs by membrane fractionation. The specific example of producing MAbs of the present invention will be described in more detail as follows: MSCs and MSC membrane proteins prepared are used alternatively for immunizing mice at a suitable interval. Mice are injected intraperitoneally with MSCs. About two weeks later, MSC membrane protein in complete Freund's adjuvant is administered intraperitoneally. After the several immunizations, mice are sacrificed. Splenocytes from mice are passed through mesh and red blood cells are removed. Primary splenocytes are fused with mouse myeloma cell line in the presence of polyethylene glycol (PEG). Hybridoma cells are screened by ELISA (enzyme-linked immunosorbent assay) and antibody-producing cells are subjected to subsequent rounds of subcloning, by limiting dilution, to obtain stable hybridomas. Positive hybridoma supernatants are harvested and screened by immunofluorescence staining and flow cytometry, finally yielding three hybridoma cell lines producing MAbs with strong reactivity to MSCs, named "YS08 hybridoma", "YS14 hybridoma" and "YS18 hybridoma", respectively, which were deposited on Dec. 10, 2005 in the International Depository Authority, the Korean Cell Line Research Foundation (Cancer Research Institute, Seoul National University, College of Medicine, 28 Yongondong, Chongno-Gu, Seoul, 110-744, Korea) and were given accession numbers KCLRF-BP-000123, KCLRF-BP-000124 and KCLRF-BP-000125, respectively.

The general procedures for monoclonal antibody production are found in Harlow, E. and Lane, D., *Antibodies: A Laboratory Manual*, Cold Spring Harbor Press, New York, 1988; Zola, H., *Monoclonal Antibodies: A Manual of Techniques*, CRC Press, Inc., Boca Raton, Fla., 1984; and Coligan, *CURRENT PROTOCOLS IN IMMUNOLOGY*, Wiley/Greene, NY, 1991, the teachings of which are incorporated herein by reference in their entity.

According to a preferred embodiment, the monoclonal antibody of this invention is YS08 produced by KCLRF-BP-000123 hybridoma, or YS14 produced by KCLRF-BP-000124 hybridoma. Particularly, monoclonal antibodies, YS08 and YS14 recognize about 130 kDa membrane protein of bone marrow-derived MSCs.

The three antibodies of this invention are found to be reactive with human MSCs, inter alia, bone marrow-derived human MSCs but not reactive with other cell types such as human bone-marrow mononuclear cells, thymocyte, and peripheral blood and tonsillar lymphoid cells. Therefore, the MAbs of this invention can bind to human MSCs, inter alia, bone marrow-derived human MSCs in a very specific manner.

In this regard, it could be appreciated that the MAbs of this invention may be useful for the isolation and characterization of MSCs.

In still another aspect of this invention, there is provided a method for identifying or isolating human mesenchymal stem cell by use of MAbs of this invention in accordance with various processes involving antigen-antibody reaction known to one skilled in the art.

According to a preferred embodiment, the method of this invention comprises the steps of: (a) contacting a biosample (e.g., a cell population unidentified) to MAbs of the present invention; and (b) detecting or isolating the antibody-antigen complex generated between MAbs of the present invention and human mesenchymal stem cells present in the biosample.

The present method may be performed pursuant to the immunoassay procedure known to one skilled in the art. The immunoassay format includes, but not limited to, radioimmunoassay, radioimmuno-precipitation, enzyme-linked immunosorbent assay (ELISA), capture-ELISA, dot blot assay, Western blot assay, inhibition or competition assay, sandwich assay, flow cytometry and immunofluorescence staining. The immunoassay procedures can be found in *Enzyme Immunoassay*, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies*, A Laboratory Manual, Cold Spring Harbor Laboratory Press, 1999.

For example, according to the radioimmunoassay method, the radioisotope (e.g., $P^{32}$ and $S^{35}$) labeled antibody may be used to identify MSCs in a biosample such as a mixed population of various cell types.

According to the ELISA method, the specific example of the present method may comprise the steps of: (i) coating a surface of a solid substrate with a biosample to be analyzed; (ii) incubating the biosample with MAb of this invention as a primary antibody; (iii) incubating the resultant of step (ii) with a secondary antibody conjugated to an enzyme catalyzing calorimetric, fluorometric, luminescence or infra-red reactions; and (iv) measuring the activity of the enzyme.

The solid substrate coated with the capturing antibody is hydrocarbon polymers such as polystyrene and polypropylene, glass, metals or gels. Most preferably, the solid substrate is a microtiter plate.

The biosample analyzed by the present method includes, but not limited to, cells isolated, primarily cultured, or sub-cultured, and cell suspensions.

The enzyme catalyzing calorimetric, fluorometric, luminescence or infra-red reactions includes, but not limited to, alkaline phosphatase, $\beta$-galactosidase, Cytochrome $P_{450}$, and horseradish peroxidase. Where using alkaline phosphatase, bromochloroindolylphosphate (BCIP), nitro blue tetrazolium (NBT) and ECF (enhanced chemifluorescence) may be used as a substrate; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine, Pierce), TMB (3,3,5,5-tetramethylbenzidine) and ABTS (2,2-Azine-di[3-ethylbenzthiazoline sulfonate]) may be used as a substrate.

According to the capture-ELISA method, the specific example of the present method may comprise the steps of: (i) coating a surface of a solid substrate with a capturing antibody which is one of MAbs (YS08, YS14 and YS18) of this invention; (ii) incubating the capturing antibody with a biosample to be analyzed; (iii) incubating the resultant of step (ii) with a detecting antibody which is one of MAbs of this invention and conjugated with a label generating a detectable signal; and (iv) detecting the signal generated from the label conjugated with the detecting antibody.

In the capture-ELISA method, two types of antibodies, i.e., capturing antibody and detecting antibody are used. As used herein, the term "capturing antibody" means an antibody capable of binding to MSCs present in biosamples. In the capture-ELISA of this invention, the capturing antibody is one of MAbs (YS08, YS14 and YS18) of this invention capable of specifically binding to a membrane antigen of MSCs.

The term "detecting antibody" means an antibody capable of binding to MSCs present in biosamples and conjugated to a label generating a detectable signal. The detecting antibody is one of MAbs (YS08, YS14 and YS18) of this invention capable of specifically binding to a membrane antigen of MSCs.

The capturing and detecting antibodies used may be the same or different from each other, preferably, different.

According to a preferred embodiment, the capturing antibody is bound to a solid substrate. Known materials of this type include hydrocarbon polymers such as polystyrene and polypropylene, glass, metals, and gels. The solid substrate may be in the form of a dipstick, a microtiter plate, a particle (e.g., bead), an affinity column and an immunoblot membrane (e.g., polyvinylidene fluoride membrane) (see U.S. Pat. Nos. 5,143,825, 5,374,530, 4,908,305 and 5,498,551). Most preferably, the solid substrate is a microtiter plate.

The detecting antibody has a label generating a detectable signal. The label includes, but not limited to, a chemical (e.g., biotin), an enzymatic (e.g., alkaline phosphatase, peroxidase, $\beta$-galactosidase and $\beta$-glucosidase), a radioactive.

(e.g., $I^{125}$ and $C^{14}$), a fluorescent (e.g., fluorescein), a luminescent, a chemiluminescent and a FRET (fluorescence resonance energy transfer) label. Various labels and methods for labeling antibodies are well known in the art (Ed Harlow and David Lane, *Using Antibodies*, A Laboratory Manual, Cold Spring Harbor Laboratory Press, 1999). Most preferably, the detecting antibody is labeled with biotin or horseradish peroxidase.

The detection of the signal generated from the label conjugated with the detecting antibody can be carried out by various processes well known in the art. The detection of the signal is indicative of the presence of mesenchymal stem cells in biosamples. This step could be carried out quantitatively or qualitatively according to conventional procedures, e.g., using various detectable label/substrate pairs as described in *Enzyme Immunoassay*, E. T. Maggio, ed., CRC Press, Boca Raton, Fla., 1980 and Ed Harlow and David Lane, *Using Antibodies*, A Laboratory Manual, Cold Spring Harbor Laboratory Press, 1999. Where the detecting antibody is labeled with alkaline phosphatase, bromochloroindolylphosphate (BCIP), nitro blue tetrazolium (NBT) and ECF (enhanced chemifluorescence) may be used as a substrate for color developing reactions; in the case of labeled with horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), TMB (3,3,5,5-tetramethylbenzidine) and ABTS (2,2-Azine-di[3-ethylbenzthiazoline sulfonate]) may be used as a substrate. Other label/substrate, pairs include biotin/streptavidin, and luciferase/luciferin.

Where the present method is carried out to isolate human mesenchymal stem cell by use of MAbs of this invention, it may be conducted in accordance with flow cytometry (Ormerod, M. G., ed. 1990, *Flow Cytometry: A Practical Approach*. IRL Press) or immunoaffinity purification (Ed Harlow and David Lane, *Using Antibodies*, A Laboratory Manual, Cold Spring Harbor Laboratory Press, 1999).

In further aspect of this invention, there is provided a kit for identifying or isolating human mesenchymal stem cell, which comprises at least one of MAbs of this invention.

The present kits may optionally include the reagents and/or devices. For example, microtiter plate, buffers, and/or substrates for color developing reaction. The MAbs of this invention may be provided in the coated form on a microtiter plate. The kit may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

The monoclonal antibodies of this invention exhibit excellent specificity to human mesenchymal stem cells, inter alia, bone marrow-derived human mesenchymal stem cells, so that it allows for the identification and isolation of human mesenchymal stem cells with much higher specificity.

The following specific examples are intended to be illustrative of the invention and should not be construed as limiting the scope of the invention as defined by appended claims.

EXAMPLES

Materials and Methods

Isolation and Culture Expansion of Bone Marrow Derived Mesenchymal Stem Cells.

BM (bone marrow) was obtained by iliac crest aspiration from normal human donors. BM was placed in a 50 mL syringe containing 5,000 units of preservative-free heparin, diluted 1:1 with phosphate buffered saline (PBS), resuspended in PBS to a final volume of 10 mL, and layered over an equal volume of Histopaque-1077 (Sigma Chemical Co., St. Louis, Mo.). After centrifugation at 2,000 rpm for 30 min, mononuclear cells were recovered from the gradient interface, rinsed twice in PBS, adjusted to a concentration of $1.5 \times 10^7$ cells, and seeded onto 100-mm culture plates in Dulbecco's Modified Eagle's Medium-Low Glucose (DMEM-LG; 1 g/L glucose, JBI, Korea) containing 1% penicillin-streptomycin (P/S; 10,000 units/ml, Gibco/BRL, NY) and 10% (v/v) heat-inactivated fetal bovine serum (FBS; Hyclone, Logan, Utah). Total numbers of nucleated and viable cells were determined using a hemocytometer using trypan blue (Gibco/BRL, Gaithersburg, Md.) staining. Cultures were maintained at 37° C. in a humidified atmosphere containing 5%. $CO_2$ with an initial medium change at day 7 and then every 3 or 4 days. On reaching 80% confluence, adherent cells were resuspended using 0.25% trypsin-EDTA (Gibco/BRL) for 5 min at 37° C. (the action of trypsin was stopped by adding one-half volume of FBS) and cells were then reseeded at $1 \times 10^6$ cells per plate.

Membrane Protein Antigen Fractionation

Antigens were prepared from MSCs by membrane fractionation. Confluent MSCs were collected and homogenized in homogenization buffer, 20 mM HEPES (pH 7.4) containing 10 mM EDTA and 250 mM sucrose. Homogenates were ultrasonicated and ultracentrifuged twice at 55,000 rpm for 2 hr at 4° C.

Immunization of Mice and Monoclonal Antibody Production

MSCs and MSC membrane proteins were used alternatively for immunizing BALB/c mice at 2-week intervals for 14 weeks. Eight week-old female BALB/c were injected intraperitoneally with 1×1 MSCs. Two weeks later 100 μg of MSC membrane protein in complete Freund's adjuvant (Qiagen, CA) was administered intraperitoneally. After the eighth immunization, mice were sacrificed on the third day. Splenocytes were passed through a wire 60-mesh and red blood cells were removed by incubating with 10 mM HEPES (pH 7.2) containing 0.83% $NH_4Cl$. Monoclonal antibodies were produced as previously described.[16] Primary splenocytes were fused with the mouse myeloma cell line $SPO_2$ (Sp20-Ag14) in the presence of polyethylene glycol (PEG; molecular wt. 1300-1600; Sigma). Hybridoma cells were screened by ELISA and antibody-producing cells were subjected to subsequent rounds of subcloning, by limiting dilution, to obtain stable hybridomas. Positive hybridoma supernatants were harvested and screened by immunofluorescence staining and flow cytometry.

Enzyme-Linked Immunosorbent Assay (ELISA)

Each well of a 96-well plate was coated with MSC membrane protein antigen in PBS (1 μg/mL, 50 μL) and cultured for 1 hr at 37° C. Culture supernatants containing MAbs were then added and incubated for 1 hr at 37° C. The wells were then washed with PBS-Tween and incubated with horseradish peroxidase (HRP)-conjugated goat anti-mouse antibodies (Ig G, A, M, KPL, Gaithersburg, Md.) for 50 min at 37° C. Following this incubation, the wells were washed with PBS solution and bound antibodies were visualized by calorimetric assay using o-phenylene diamine (Sigma) as a chromogenic substrate. Absorbance was read using a microplate reader at 492 nm.

Isotyping of MAbs

The classes and subclasses of these MAbs were determined by enzyme immunoassay using an ImmunoPure Monoclonal Antibody Isotyping Kit I (Pierce, Rockford, Ill.).

Immunofluorescence Staining

MSCs were adhered to spot slide bottoms and fixed with −20° C. methanol (100%) for 5 min. Cells were then rehydrated by incubation in PBS for 5 min at room temperature, washed three times with PBS, blocked with 3% bovine serum albumin in PBS and incubated overnight at 4° C. with hybridoma supernatants containing MAbs. Primary antibodies were removed by washing three times with PBS and cells were incubated with fluorescein isothiocyanate (FITC)-conjugated goat anti-mouse antibodies (DiNonA Inc., Seoul, Korea) for 1 hr at room temperature. Secondary antibodies were removed by washing three times with PBS. Coverslips were mounted onto slides with a solution containing 500% PBS and 50% glycerol. Labeled cells were observed under an Axiovert 200 (Zeiss, Thornwood, NY).

Flow Cytometry

Flow cytometry was performed to screen MSCs, human tumor cell lines (HT-29, Jurkat, MCF-7, Molt-4, TF-1 and U-937 from American Type Culture Collection, ATCC, Rockville, Md.), and a hematopoietic stem cell line (KG-1, ATCC) for MAbs. Cells were permeabilized with ice cold 75% methanol in PBS for 30 min, washed once, incubated with hybridoma supernatant for 30 min at 4° C., and washed three times. A FITC-conjugated rabbit anti-mouse IgG (Jackson ImmunoResearch, West Grove, Pa.), diluted 1:1000 in PBS, was then added, and cells were incubated for 1 hr at 4° C. Cells were analyzed within 2 hr after staining using a flow cytometer (FACScalibur, Becton Dickinson). A total of $1 \times 10^6$ cells were collected for each measurement. Negative control samples were stained with isotype-matched irrelevant MAb.

Western Blotting

Protein expressions were measured by Western blotting. Cells were washed twice with ice-cold PBS, scraped into microfuge tubes, pelleted by centrifugation, and suspended in PRO—PREP™ protein extraction buffer (Intron, Seongnam, Korea). After 30 min of incubation on ice, samples were centrifuged at 14,000 rpm for 30 min at 4° C. Protein concentrations were measured using Bio-Rad Protein Assay reagent (Bio-Rad, Hercules, Calif.) with bovine serum albumin as standard. Sodium dodecyl sulfate-polyacrylamide gel electrophoresis (SDS-PAGE) was carried out using a mini-protein system (Bio-Rad). Dissolved protein samples were combined with sample buffer (125 mM Tris, pH 6.8, 5% glycerol, 2% SDS, 1% 2-mercaptoethanol and 0.006% bromophenol blue) and boiled for 5 min at 100° C., and cooled instantly. Equivalent amounts of protein samples (40 μg/lane) were loaded onto 12% SDS gel (1.5 mm 10 wells; Bio-Rad). Molecular weight markers (Kaleidoscope Prestained Standards, Bio-Rad) were run on the same gel. Electrophoresis was carried out in a running buffer at 100 V for 60 min. Proteins were transferred from gel onto polyvinylidene difluoride (PVDF) membranes (Millipore, Bedford, Mass.) (90 min at 30 V) in transfer buffer (192 mM glycine, 25 mM Tris-HCl, pH 8.3, 0.02% SDS, and 20% v/v methanol) in a Trans-Blot apparatus (Bio-Rad). Nonspecific binding sites were blocked with 5% (w/v) non-fat dried milk in TBS-Tween buffer (20 mM Tris, pH 8.0, 150 mM NaCl, and 0.1% Tween 20) for 1 hr at room temperature. Membranes were then washed twice for 10 min in TBS-Tween buffer and then incubated with hybridoma supernatants containing MAbs overnight at 4° C. Membranes were then washed three times with TBS-Tween buffer for 10 min each time, and incubated with HRP-conjugated rabbit anti-mouse IgG polyclonal antibodies (1: 1000, Jackson ImmunoResearch) in TBS-Tween buffer containing 1% non-fat dried milk for 2 hr at room temperature. After washing chemiluminescent substrate (Amersham Life Science, Arlington Heights, Ill.) was added and incubation continued for 10 min. Blots were then exposed to radiographic film.

Results

Cultures of Human MSCs and its Phenotype

Human bone marrow-derived MSCs were cultured and expanded. Colonies were observed at approximately 7 days after initial plating. A morphologically homogeneous population of fibroblast-like cells with 90% confluence was obtained after 2 weeks (FIG. 1A). The cells were replated into culture dishes and cultured for 2 weeks. The replated cells were used for subsequent experiments. The cultured MSCs were positive for CD105 and CD166, but negative for CD34 by flow cytometry FIG. 1B), which is consistent with the human MSCs phenotype and excluded the contamination of hematopoietic stem cells.

MAbs against Human MSCs

Figure 2:
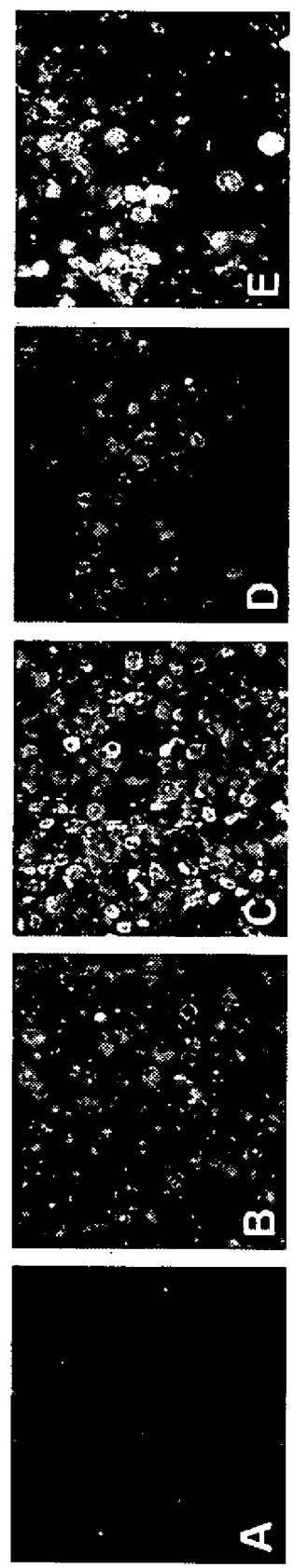
FIG. 2 represents immunofluorescence of human bone marrow-derived mesenchymal stem cells using monoclonal antibodies. Original magnification, ×200. (A) Control, (B) YS08, (C) YS14, (D) YS18, (E) SH2.

MAbs against MSCs were produced and screened using conventional cell fusion and enzyme-linked immunosorbent assay (ELISA). After fusion, the resultant hybrids were selected by ELISA, cloned and maintained in culture in vitro. In initial screening by ELISA, 33 MAbs which were reactive with the MSC antigen were cloned. Immunofluorescence staining and flow cytometric analysis were performed after final cloning. Ten MAbs exhibited bright staining of individual cell by immunofluorescence staining. Among these, three clones showing strong reaction with MSCs were selected for next experiments (named YS08, YS14, and YS18). The typical immunofluorescence staining patterns are showed in FIG. 2. The isotype of these 3 MAbs was determined by enzyme immunoassay using hybridoma culture supernatant. All 3 MAbs had the IgM and kappa light chain (data not shown). Three hybridoma cell lines producing 3 MAbs showing strong reaction with MSCs were denoted as "YS08 hybridoma", "YS14 hybridoma" and "YS18 hybridoma", respectively, which were deposited on Dec. 10, 2005 in the International Depository Authority, the Korean Cell Line Research Foundation (Cancer Research Institute, Seoul National University, College of Medicine, 28 Yongondong, Chongno-Gu, Seoul, 110-744, Korea) and were given accession numbers KCLRF-BP-000123, KCLRF-BP-000124 and KCLRF-BP-000125, respectively.

FACS Profiles of YS08, YS14 and YS18

Figure 3:
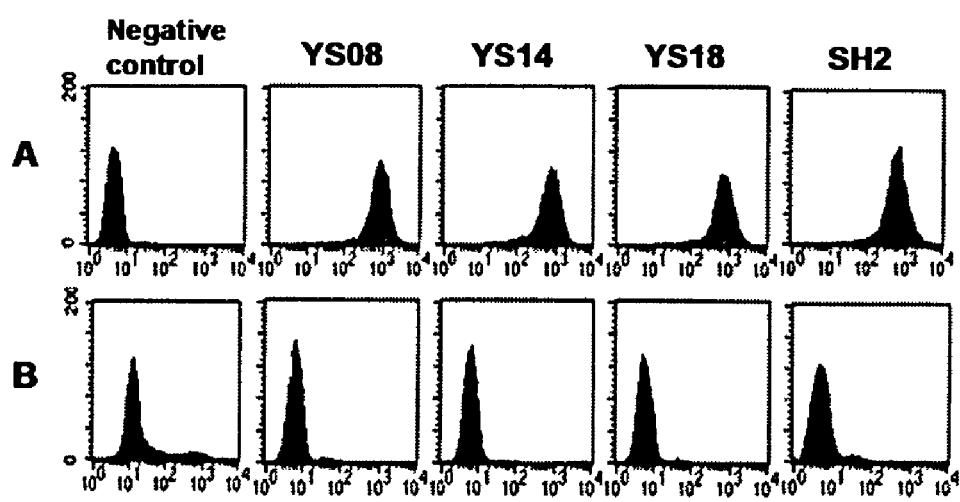
FIG. 3 shows flow cytometric analysis of mesenchymal stem cells (A), and bone marrow derived mononuclear cells (B) for the expressions of YS08, YS14, and YS18.

Bone marrow-derived mononuclear cells, peripheral mononuclear cell, and cultured-MSCs were analyzed using these three MAbs. Additionally, several human tumor cell lines were analyzed. Cultured MSCs were strong positive to these 3 MAbs (YS08, YS14, and YS18) (FIG. 3A), and bone marrow-derived mononuclear cells did not react with these MAbs by flow cytometry (FIG. 3B). Human thymocytes, peripheral blood and tonsillar lymphoid cells were all negative to these MAbs (data not shown). All tested cells were negative, and listed in the Table 1 with origins of cell line.

TABLE 1

Flow cytometric analysis patterns in human tumor cell lines

| Cell lines | | Flow cytometric analysis of MAbs | | |
|---|---|---|---|---|
| Name | Origin | YS08 | YS14 | YS 18 |
| HT-29 | Colorectal adenocarcinoma | — | — | — |
| KG-1 | Acute myelogenous leukemia | — | — | — |
| Jurkat | Acute T cell leukemia | — | — | — |
| MCF7 | Breast adenocarcinoma | — | — | — |
| MOLT-4 | Acute T-lymphoblastic leukemia | — | — | — |
| TF-1 | Erythroleukemia | — | — | — |
| U-937 | Histiocytic lymphoma | — | — | — |

The cells were obtained from American Type Culture Collection, Rockville, MD. Reactivity in flow cytometry denoted as "—" (<5-10%).

Western Blotting

Figure 4:
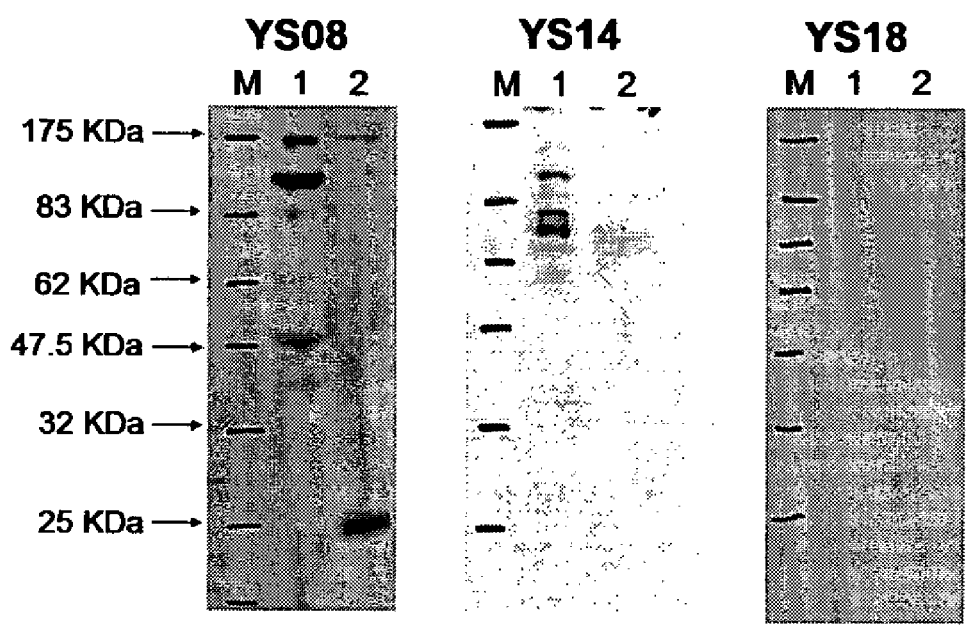
FIG. 4 shows Western blotting results of monoclonal antibodies against mesenchymal stem cell antigens. (YS08, YS14, and YS18). M: size marker, lane 1: mesenchymal stem cells, lane 2: thymocytes as negative control.

To characterize the biochemical nature of antigens recognized by these MAbs, Western blotting was carried out with cultured MSCs lysates and thymocytes lysates. Two hybridomas (YS08 and YS14) showed bands in Western blotting. Multiple bands of molecular weights ranging from 32 to 175 kDa were shown (FIG. 4). Although it was expected that a single band would be recognized by each monoclonal antibody, hybridoma culture supernatants recognized more than one band or no band in. Western blotting. A possible explanation for this could be protein cleavage during the antigen preparation step. Moreover, MAbs may recognize common antigens of isoforms, or may nor recognize antigens due to denaturation of the conformational epitope.

The antigen detected by MAbs (YS08 and YS14) might have the size of about 130 kDa, since this band was repetitively noted in MSCs but not in other cell lysates such as thymocytes or tumor cell lines. YS18 did not react in Western blotting.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Tavassoli M, and Minguell J J: Homing of hematopoietic progenitor cells to the marrow. Proceedings of the Society for Experimental Biology and Medicine. 1991, pp. 367-373,
2. Tavassoli M, and Minguell J J: Hematopoiesis: how does it happen? Current Opinion in Cell Biology. 1995, pp. 8:70-877.
3. Pittenger M F, Mackay A M, Beck S C, Jaiswal R K, Douglas R, Mosca J D, Moorman. M A, Simonetti D W, Craig S, and Marshak D R: Multilineage potential of adult human mesenchymal stem cells. Science 1999; 284:143-147.
4. Prockop D J: Marrow stromal cells as stem cells for non-hematopoietic tissues. Science 1997; 276:71-74.
5. Phinney D G, Kopen G, Isaacson R L, and Prockop D J: Plastic adherent stromal cells from the bone marrow of commonly used strains of inbred mice; variations in yield, growth, and differentiation. J Cell Biochem 1999; 72: 570-585.
6. Jaiswal N, Haynesworth S E, Caplan A I, and Bruder S P: Osteogenic differentiation of purified culture expanded human mesenchymal stem cells in vitro. J Cell Biochem 1997; 64:295-312.
7. Johnstone B, Gering T M, Caplan A I, Goldberg V M, and Yoo J U: In vitro chondrogenesis of bone marrow derived mesenchymal progenitor cells. Exp Cell Res 1998; 238: 265-272.
8. Young R G, Butler D L, Weber W, Caplan A I, Gordon S L, and Fink D J: The use of mesenchymal stem cells in a collagen matrix for Achilles tendon repair. J Orthop Res 1998:16; 406-413.
9. Wakatani S, Saito T, and Caplan A I: Mygenic cells derived from rat bone marrow mesenchymal stem cells exposed to 5-azacytidine. Muscle Nerve 1995; 18:1417-1426.
10. Hynesworth S E, Goshima J, Goldberg V M, and Caplan A I: Characterization of cells with osteogenic potential from human marrow. Bone 1992; 13: 81-88.
11. Friedenstein A J, Gorskaja J F, and Kulagina N N: Fibroblast precursors in normal and irradiated mouse hematopoietic organs. Exp Hematol 1976; 4:267-274.
12. Conget P A, and Minguell J J: Phenotypical and functional properties of human bone marrow mesenchymal progenitor cells. J Cel Physiol 1999; 181:67-73.
13. Haynesworth S E, Baber M A, and Caplan A I: Cytokine expression by human marrow-derived mesenchymal progenitor cells in vitro: effects of dexamethasone and IL-1α. J Cell Physiol 1996; 166:585-592.
14. Majumdar M K, Thiede M A, Mosca J D, Moonman M, and Gerson S L: Phenotype and functional comparison of cultures of marrow-derived mesenchymal stem cells (MSCs) and stromal cells. J Cell Physiol 1998; 17:57-66.
15. Haynesworth S E, Baber M A, and Caplan A I: Cell surface antigens on human marrow-derived mesenchymal cells are detected by monoclonal antibodies. Bone 1992; 13:69-80.
16. Chung H G and Rhee S G: Separation of glutamine synthetase species with different states of adenylylation by chromatography on monoclonal anti-AMP antibody affinity columns. Proc Natl Acad Sci 1984; 81:4677-4681.
17. Clark B R, and Keating A: Biology of bone marrow stroma. Ann NY Acad Sci 1995; 770:70-78.
18. Long M W, Robinson J A, and Ashcraft E A. Regulation of human bone marrow-derived osteoprogenitor cells by osteogenic growth factors. J Clin Invest 1995; 95:881-887.
19. Joyner C J, Bennett A, and Triffitt J T: Identification and enrichment of human osteoprogenitor cells by using differentiation stage-specific mAbs. Bone 1997; 21:1-6.
20. Haynesworth S E, Barer M A, and Caplan A I: Cell surface antigens on human marrow-derived mesenchymal cells are detected by monoclonal antibodies. Bone 1992; 13:69-80.
21. Cheng L, Qasba P, Vanguri P, and Thiede M A: Human mesenchymal stem cells support megakaryocyte and proplatelet formation from CD34+ hematopoietic progenitor cells. J Cell Physiol 2000; 184:58-69.

What is claimed is:

1. A monoclonal antibody specifically binding to a membrane protein antigen of human mesenchymal stem cells, which is produced by a hybridoma cell line as deposited with the Korean Cell Line Research Foundation under Accession Nos. KCLRF-BP-000123, KCLRF-BP-000124 or KCLRF-BP-000125.

2. A hybridoma cell line producing the monoclonal antibody of claim 1, which is deposited with the Korean Cell Line Research Foundation under Accession Nos. KCLRF-BP-000123, KCLRF-BP-000124 or KCLRF-BP-000125.

3. A method for identifying or isolating human mesenchymal stem cells, which comprises the steps of:
(a) contacting a biosample to the monoclonal antibody of claim 1; and
(b) detecting or isolating an antibody-antigen complex generated between the monoclonal antibody of claim 1 and human mesenchymal stem cell present in the biosample.

* * * * *